(12) United States Patent
Yen

(10) Patent No.: US 7,314,954 B1
(45) Date of Patent: Jan. 1, 2008

(54) SYSTEM AND METHOD FOR RECOVERING PTA MOTHER LIQUID AND PURIFYING AND REGENERATING OF CATALYST

(75) Inventor: David Yen, Tao-Yuan Hsien (TW)

(73) Assignee: Mechema Chemicals International Corp., Tao-Yuan Hsien (TW)

( * ) Notice: Subject to any disclaimer, the term of this patent is extended or adjusted under 35 U.S.C. 154(b) by 0 days.

(21) Appl. No.: 11/558,020

(22) Filed: Nov. 9, 2006

(51) Int. Cl.
    *C07C 51/16* (2006.01)
(52) U.S. Cl. .................. 562/414; 562/412; 562/485
(58) Field of Classification Search ............... 562/414, 562/485, 412
    See application file for complete search history.

(56) References Cited

U.S. PATENT DOCUMENTS 5,955,394 A * 9/1999 Kelly ......................... 502/12

* cited by examiner

*Primary Examiner*—Yvonne Eyler
*Assistant Examiner*—Sudhakar Katakam
(74) *Attorney, Agent, or Firm*—Ming Chow; Sinorica, LLC

(57) ABSTRACT

A system and a method for recovering PTA (purified terephthalic acid) mother liquid as well as purifying and regenerating catalyst, the system and the method is used mainly in manufacturing PTA wherein the mother liquid of the PTA generated by hydrogenation reaction is recovered by means of a PTA mother liquid recovering system to produce cobalt containing inorganic acid solution which is passed through a catalyst purifying/regenerating system and is electrolyzed with a cobalt purifying/regenerating system to produce metal cobalt which is then passed through an oxidized catalyst producing system to produce oxidized catalyst to be circulated for use in the process of manufacturing PTA.

26 Claims, 6 Drawing Sheets

SYSTEM AND METHOD FOR RECOVERING PTA MOTHER LIQUID AND PURIFYING AND REGENERATING OF CATALYST

BACKGROUND OF THE INVENTION

1. Field of the Invention

The present invention relates to a system and a method for recovering PTA (purified terephthalic acid) mother liquid and purifying and regenerating of catalyst, being used in manufacturing PTA; and especially relates to a system and a method wherein in the process of manufacturing PTA, the cobalt ions in the mother liquid of the PTA generated by hydrogenation reaction are adsorbed by using anion exchange resin, and the cobalt ions adsorbed by the resin are changed over to form cobalt containing inorganic acid solution by using inorganic acid, the cobalt containing inorganic acid solution thereafter is used to manufacture metallic cobalt after being processed by purifying and regenerating of catalyst, and then the metallic cobalt is used to regenerate oxidized catalysts.

2. Description of the Prior Art

A method of producing purified terephthalic acid (PTA) uses para-xylene (PX) as raw material to produce a kind of white powder of the purity of 99.95% through the reaction processes of oxidation and hydrogenation (refining). PTA is one of the main raw materials for manufacturing polyester fiber for making polyester containers (such as PET bottles), plastic for engineering and plaster.

In the process of oxidation, oxidized catalysts containing ions of cobalt, manganese and bromine are wanted and added, and cobalt and manganese ions of two valences are used as catalysts, bromine ion is used as initiating agent. In the process of hydrogenation, crude terephthalic acid (CTA) is pulped and mixed, then hydrogen is added therein to react with palladium catalyst under high temperature and high pressure, 4-carboxyl benzaldehyde (4-CBA) impurity contained therein is reduced to water soluble p-toluic acid, and is produced to form PTA after centrifugation, water washing, filtering, separating and crystal drying.

By virtue that ash contained in the crude terephthalic acid (CTA) is heavy metal ions having limited amount of 200 ppm, after centrifugation, water washing, filtering and separating, the PTA (purified terephthalic acid) mother liquid discharged contains therein about 15-25 ppm metal cobalt ions. This mother liquid of PTA containing therein metal cobalt ions is unable to be recovered for reusing in the process of manufacturing and must be discharged. Such situation will increase the burden of water treatment equipment in a subsequent stage. If the metal cobalt ions in the mother liquid of PTA can be recovered, the mother liquid of PTA can be recovered for reusing; this can largely lower the amount of water used, and an object of saving cost can be achieved.

SUMMARY OF THE INVENTION

The object of the present invention is to provide a system and a method for recovering PTA (purified terephthalic acid) mother liquid as well as purifying and regenerating of catalyst, the system and the method are used mainly in manufacturing PTA wherein the mother liquid of the PTA generated by hydrogenation reaction is recovered by means of a PTA mother liquid recovering system to produce cobalt containing inorganic acid solution which is passed through a catalyst purifying/regenerating system and is electrolyzed with a cobalt purifying regenerating system to produce metal cobalt which is then passed through an oxidized catalyst producing system to produce oxidized catalyst to be circulated for use in the process of manufacturing PTA.

In recovering the PTA mother liquid, the PTA (purified terephthalic acid) mother liquid is passed through an anion exchange resin column to remove the metal cobalt ions contained therein, then inorganic acid solution is passed through the column for regeneration, the inorganic acid regeneration solution is sent to a catalyst purifying/regenerating system to convert the metal cobalt ions into regenerated metal.

The PTA mother liquid recovering method of the present invention includes the following steps:

a) The PTA mother liquid is filtered for separation mainly of solid organic materials from liquid to avoid the solid materials from entering an ion exchange reacting tank to create clogging of pipe lines or a resin tank;

b) the liquid separated is heated, it is passed through a heat exchanger to raise its temperature for 5~10° C., raising of temperature can increase the solubility of the organic materials in water to avoid crystal segregation by temperature lowering in a subsequent stage process of manufacturing;

c) the cobalt ions in the liquid is adsorbed with anion exchange resin till being saturated;

d) the resin is regenerated with inorganic alkali, if there is organic material attached to the surfaces of granules of the resin during the process of exchanging of anion exchange resin, the inorganic alkali is used to purify the resin to remove the organic material on the surfaces;

e) inorganic acid is used to take off by changing over all the cobalt ions adsorbed by the resin to form inorganic acid solution containing cobalt; thus recovering of the PTA mother liquid is completed.

The method of recovering PTA mother liquid provided by the present invention further includes the subsequent steps:

f) a catalyst regenerating system is used to convert the inorganic acid solution into metal cobalt;

g) an oxidized catalyst producing system is used to produce the oxidized catalyst in the process of manufacturing PTA by using the metal cobalt.

Waste water created in adsorbing cobalt ions with anion exchange resin is purified with an R.O. reverse osmotic waster water treating system, the waster water with increased concentration is discharged to a waste water pool for treating, regenerated water is generated after purification and can be circulated for reusing.

The present invention is characterized mainly in that:

1) The resin is cleansed with inorganic alkali, by exchange of metal ions with $H^+$ ions of the resin during the process of exchanging of anion, the PH value of the surface of the resin is lowered, this results sedimentation of organic acids (such as terephthalic acid, o-phthalic acid, iso-phthalic acid, benzoic acid, p-toluic acid, 4-carboxyl benzaldehyde) to envelope the resin, therefore the step d) is necessary to assure regular use of the resin.

2) Catalysts collected in the present invention do not use an HBr direct recovering system; this is mainly because of avoiding generating catalysts with high free acids to damage the reactor.

3) The reaction of PTA is proceeded to under high temperature and acids, hence the reactor and pipelines will have other impurities (such as Fe, Zn, Ca, Mg, Na, Ni, Cr, Cu and Pb), accumulation of impurities will be resulted if the catalysts collected are directly sent back to the PTA reacting system, thereby the present method shall specifically go through a catalyst purifying/regenerating system to produce pure catalysts which can then be sent back to the PTA reacting system.

According to the above stated steps, the present invention can provide a PTA mother liquid recovering system that includes: a filtering device connecting to the PTA mother liquid, a heat exchanger, an anion exchange resin column, an inorganic alkali regenerating device, an inorganic acid changing over device, a catalyst purifying/regenerating system, an oxidized catalyst reproducing system and a waste water treating system.

Besides, in the system and the method of catalyst purifying/regenerating provided in the present invention, particularly in the system and the method of purifying/regenerating for cobalt, the PTA mother liquid is collected with the PTA mother liquid recovering system to produce cobalt containing inorganic acid solution which is passed through the process of manufacturing of the present invention to purify and regenerate metal cobalt with high purity and extremely few impurities to be provided for the subsequent oxidized catalyst producing system to reproduce oxidized catalyst which is circulated for use in the process of oxidation.

The method of cobalt purifying/regenerating provided in the present invention includes the following steps: an acid solution step, a neutralization and sedimentation step, a resin treatment step, a metal extraction step and an electrolyzing step, in order to purify the metal salt and cobalt containing inorganic acid solution and to regenerate metal cobalt.

According to the method of the present invention, a cobalt purifying/regenerating system can be provided to be applied to the manufacturing process of PTA for recovering and regenerating catalyst after oxidation.

The method of the present invention is applied particularly to obtain metal cobalt via the electrolyzing step, its impurities have better purity, and will not create accumulation of the impurities during circulation in manufacturing oxidized catalyst for use; its effect of recovering is better than that of a conventional chemical method in recovering catalyst.

The method and the system of the present invention will be apparent after reading the detailed description of the preferred embodiment thereof in reference to the accompanying drawings.

DETAILED DESCRIPTION OF THE PREFERRED EMBODIMENT

Figure 1:
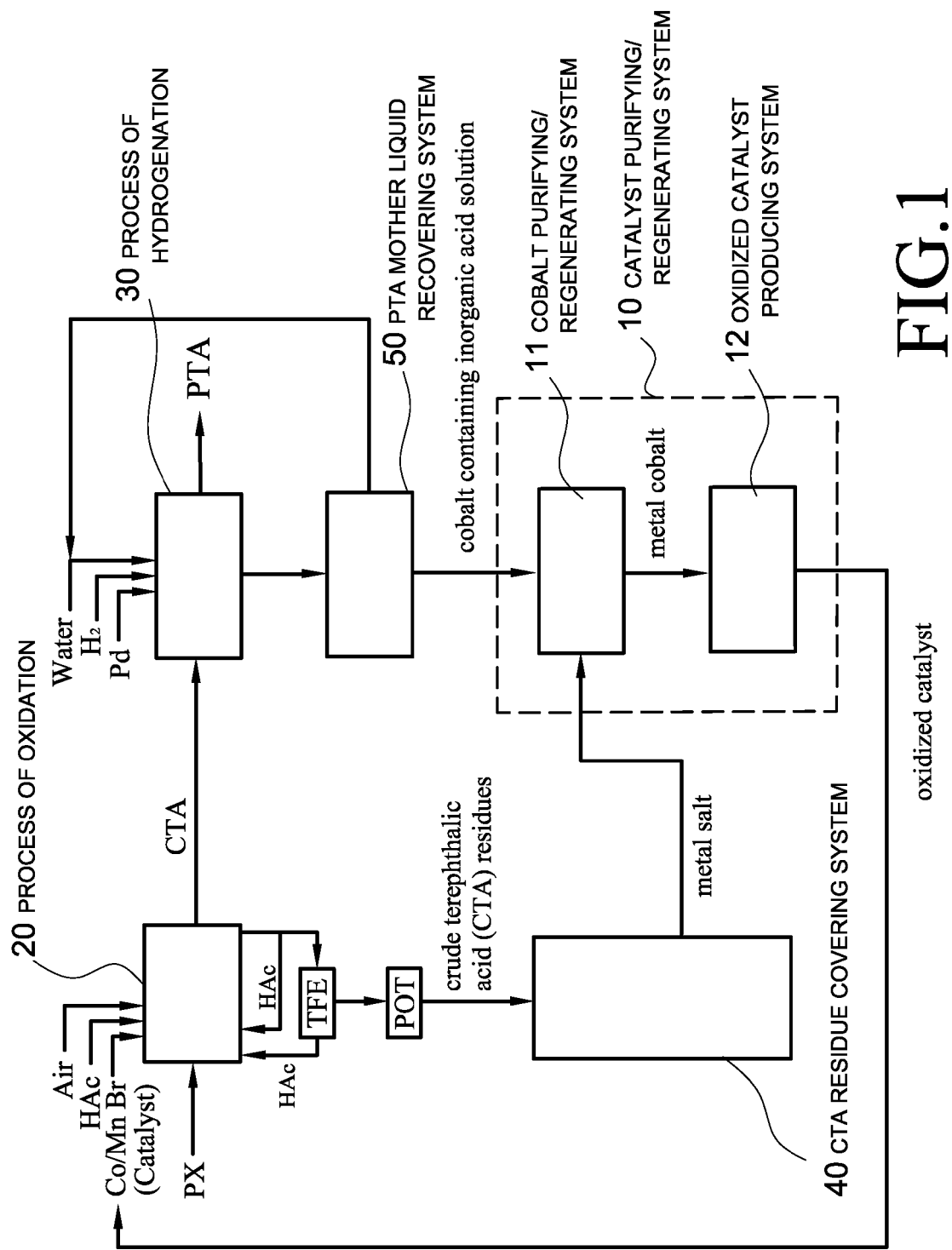
FIG. 1 is a schematic block diagram showing the system allocation and process of manufacturing during recovering PTA (purified terephthalic acid) mother liquid and purifying and regenerating of catalyst of the present invention.
Figure 2:
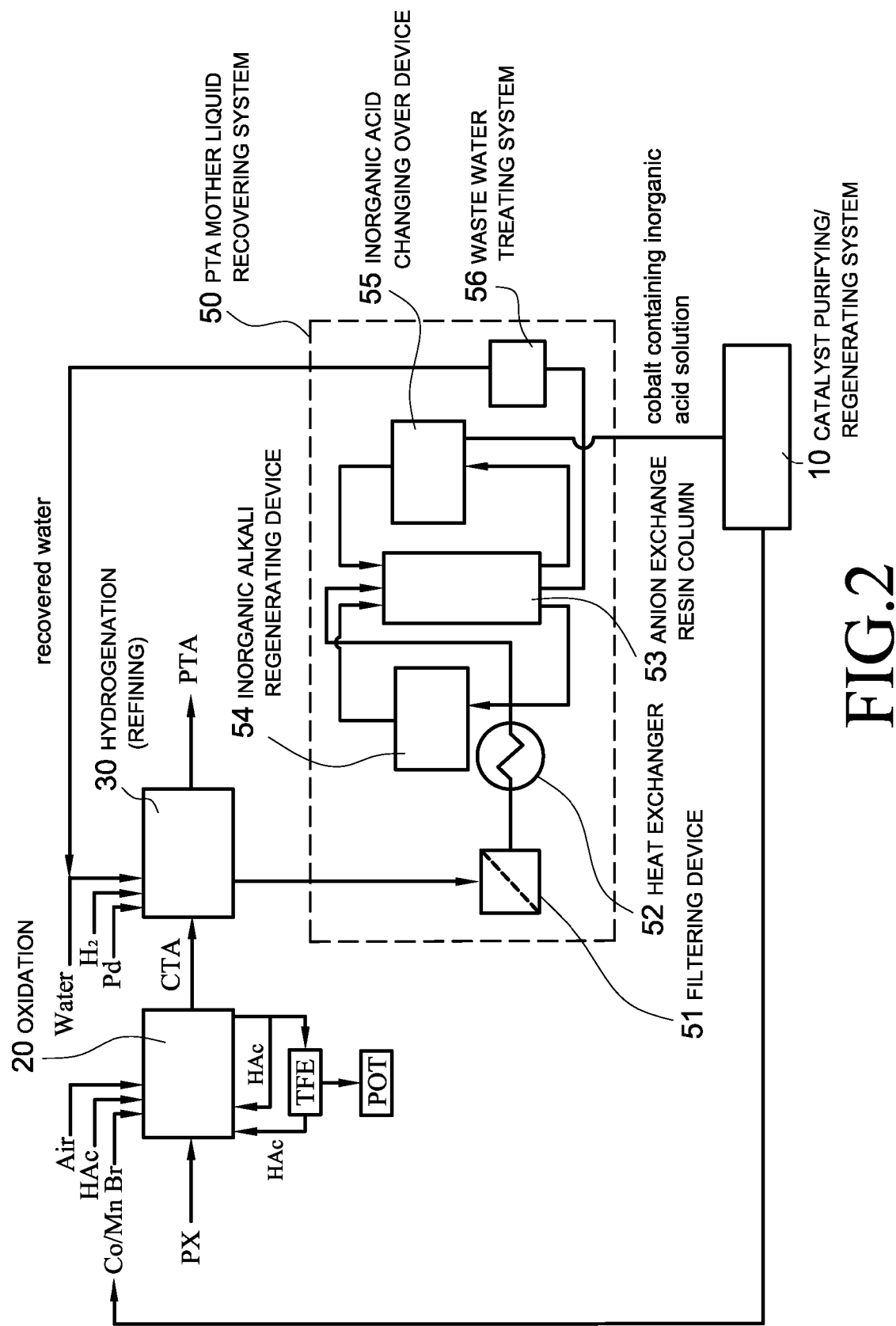
FIG. 2 is a schematic block diagram showing the allocation of the PTA (purified terephthalic acid) mother liquid recovering system of the present invention.

Referring to FIG. 1, the method of producing purified terephthalic acid (PTA) uses para-xylene (PX) as raw material to produce a kind of white powder of the purity of 99.95% through a reaction process of oxidation 20 and a reaction process of hydrogenation (refining) 30.

In the process of oxidation 20, oxidized catalysts containing the ions of cobalt, manganese and bromine are wanted and added, and cobalt and manganese ions of two valences are used as catalysts, bromine ion is used as initiating agent. The main reaction is as below: to blow air into a reactor of oxidation to mix with the para-xylene, catalysts and acetic acids (HAc), and to proceed to oxidation of the mixed solution under the pressure of 16.5 kg/cm$^2$ and 204° C. to produce crude terephthalic acid (CTA).

The residues of the crude terephthalic acid (CTA) are recovered with a crude terephthalic acid (CTA) residue recovering system to make metal salt.

In the process of hydrogenation 30, crude terephthalic acid (CTA) is pulped and mixed, then hydrogen is added therein to react with palladium catalyst under high temperature and high pressure, 4-carboxyl benzaldehyde (4-CBA) impurity contained therein is reduced to water soluble p-toluic acid, and is produced to form PTA after centrifugation, water washing, filtering, separating and crystal drying.

A PTA mother liquid recovering system 50 of the present invention includes: a filtering device 51 connecting to the PTA mother liquid, a heat exchanger 52, an anion exchange resin column 53, an inorganic alkali regenerating device 54, an inorganic acid changing over device 55 and a waste water treating system 56.

The PTA mother liquid recovering system 50 is used to change over PTA to form cobalt containing inorganic acid solution which is passed through a catalyst purifying/regenerating system to produce oxidized catalyst for the process of manufacturing PTA, the oxidized catalyst is circulated for use in the process of oxidation 20.

Figure 3:
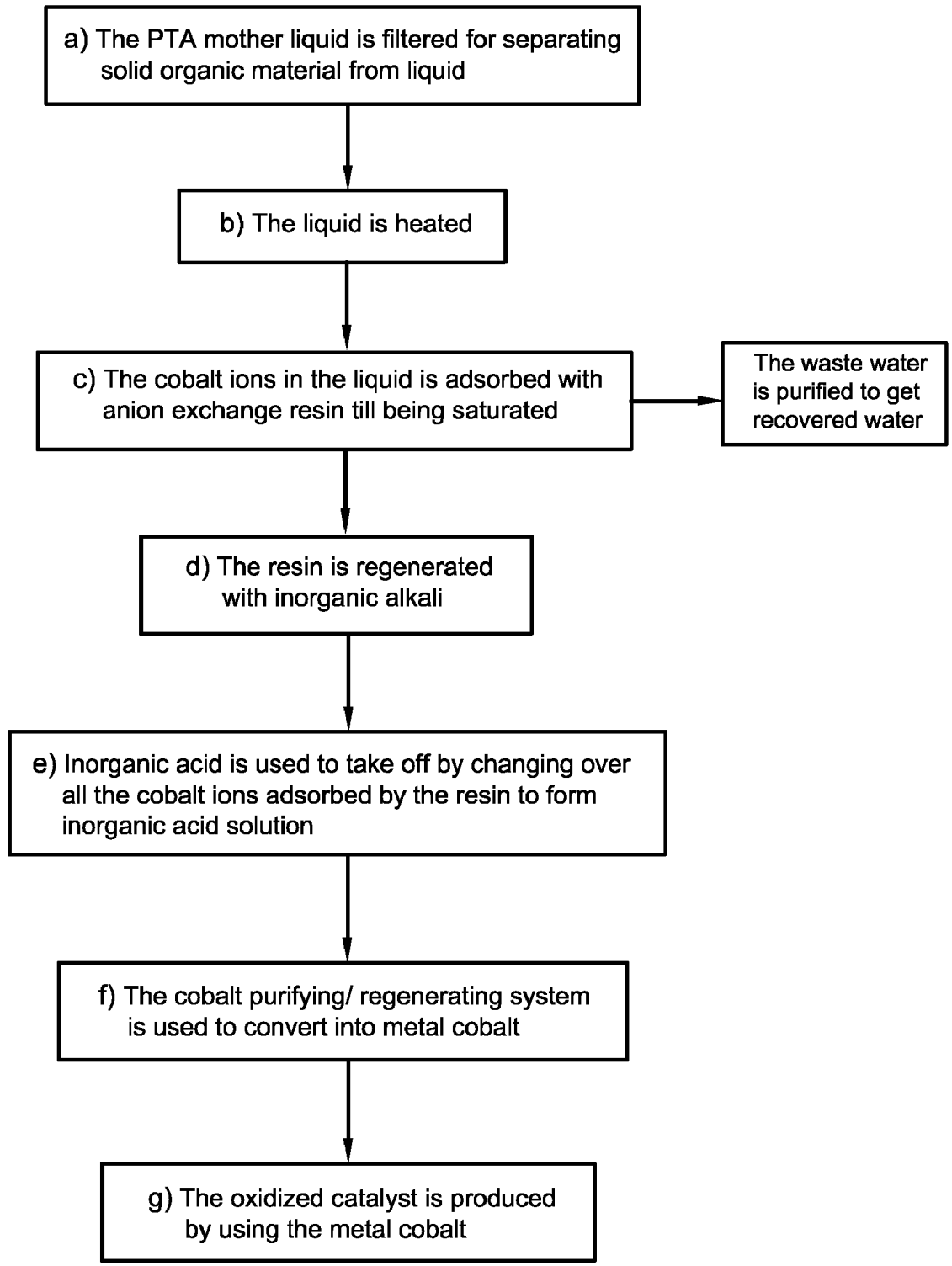
FIG. 3 is a process flow diagram showing the method of recovering PTA (purified terephthalic acid) mother liquid of the present invention.

Referring to FIG. 3, the PTA mother liquid recovering method of the present invention includes the following steps:

a) The PTA mother liquid is filtered with the filtering device 51 for separation mainly of solid organic materials from liquid to avoid the solid materials from entering an ion exchange reacting tank to create clogging of pipe lines or a resin tank;

b) the liquid separated is heated, it is passed through the heat exchanger 52 to raise its temperature for 5~10° C., raising of temperature can increase the solubility of the organic materials in water to avoid crystal segregation by temperature lowering in a subsequent stage process of manufacturing;

c) the cobalt ions in the liquid are adsorbed with anion exchange resin till being saturated;

d) the resin is generated with inorganic alkali, if there is organic material attached to the surfaces of granules of the resin during the process of exchanging of anion exchange resin, the inorganic alkali is used to regenerate the resin to remove the organic material on the surfaces;

e) when the resin adsorbs cobalt ions till being saturated, the inorganic acid changing over device 55 and the anion exchange resin column 53 are used to render the inorganic acid to take off by changing over all the cobalt ions adsorbed by the resin to form inorganic acid solution containing cobalt; thus recovering of the PTA mother liquid is completed;

f) a cobalt purifying/regenerating system 11 of the catalyst purifying/regenerating system 10 is used to convert the inorganic acid solution into metal cobalt;

g) an oxidized catalyst producing system 12 is used to produce the oxidized catalyst in the process of manufacturing PTA by using the metal cobalt.

In the PTA mother liquid recovering method of the present invention, waste water created in the anion exchange resin column 53 is purified with an R.O. reverse osmotic waste water treating system 56, the waste water with increased concentration is discharged to a waste water pool for treating, regenerated water generated after purification can be circulated for reusing.

One thing is worth noticing, the filtering method of the filtering device 51 in the present invention is but is not limited to: bag type filtering, plate type filtering, cross-flow filtering, centrifugation filtering, Dorr type, hydracyclone or hyperflux type filtering. And filtrant of the filtering device 51 includes but is not limited to: terephthalic acid, o-phthalic acid, iso-phtalic acid, benzoic acid, p-toluic acid or 4-carboxyl benzaldehyde.

The heat exchanger 52 can be but is not limited to: a shell and tube type heat exchanger, a plate type heat exchanger, a plate coil type heat exchanger, a vortex heat exchanger or a sleeve type heat exchanger.

In the PTA mother liquid recovering system 50 of the present invention, resin in the anion exchange resin column 53 includes but is not limited to: strong acidic anion exchange resin, weak acidic anion exchange resin or chelate resin.

The inorganic acid solution used in the PTA mother liquid recovering method of the present invention can be selected from but is not limited to: chlorhydric acid, hydrobromic acid or sulfuric acid; while the inorganic alkali is selected from but not limited to: sodium hydroxide, potassium hydroxide or sodium carbonate.

Figure 7:
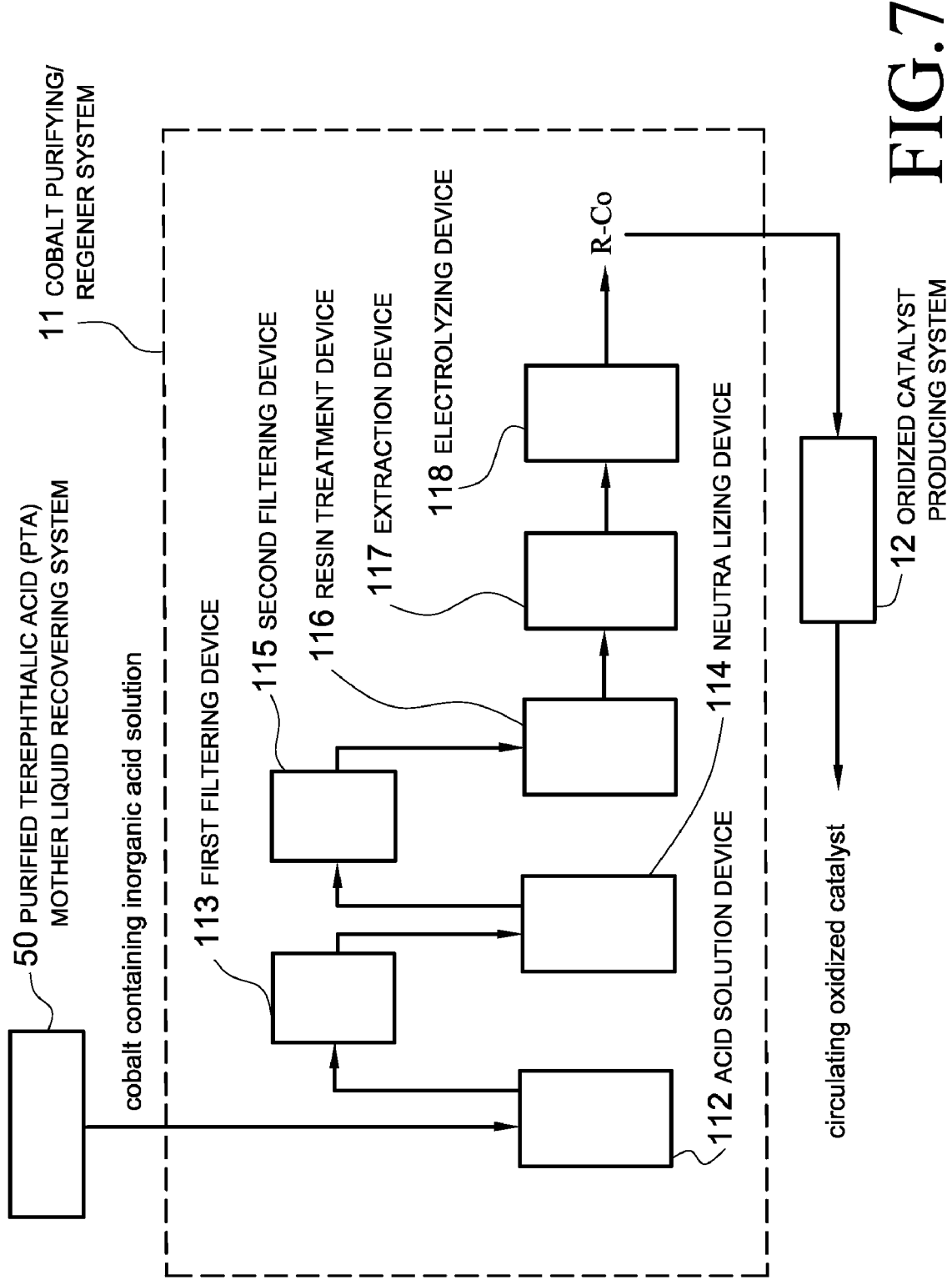
FIG. 7 is a schematic block diagram showing the allocation of the system of purifying and regenerating of catalyst of the present invention.

The catalyst purifying/regenerating system 10 of the present invention, as shown in FIGS. 1 and 7, mainly includes the cobalt purifying/regenerating system 11 and the oxidized producing system 12.

Figure 4:
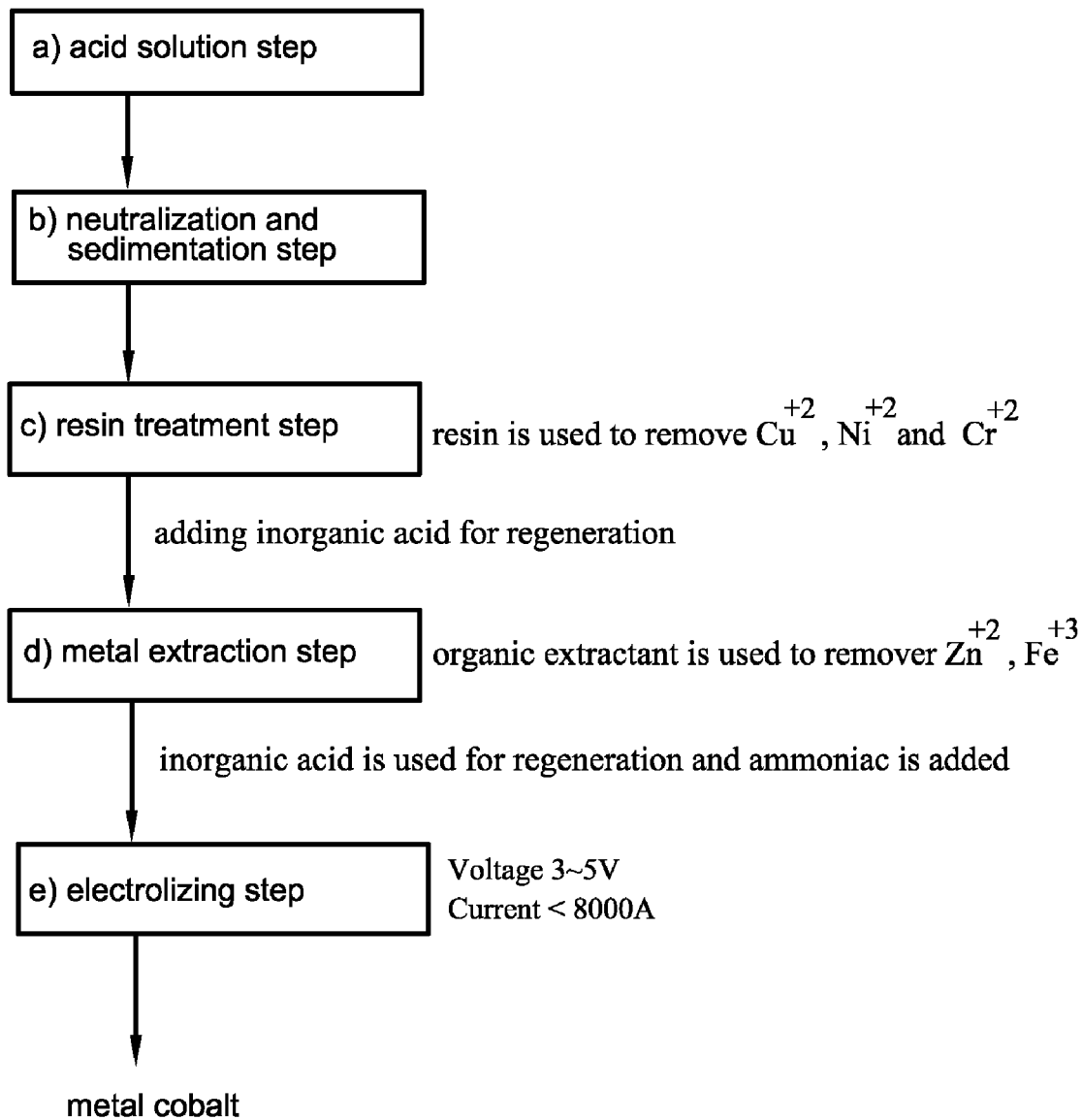
FIG. 4 is a process flow diagram showing the method of purifying and regenerating of catalyst of the present invention.

The steps of cobalt purifying/regenerating method in the catalyst purifying/regenerating system 10, as shown in FIG. 4, include: a) an acid solution step, b) a neutralization and sedimentation step, c) a resin treatment step, d) a metal extraction step and e) an electrolyzing step, with an object of manufacturing metal cobalt of high purity and low impurity.

Figure 5:
FIG. 5 is a process flow diagram showing the step of acid solution action in the method of purifying and regenerating of catalyst of the present invention.

Referring to FIG. 5, the acid solution step includes acid solution, adding oxidant and first time filtering.

The object of acid solution mainly is to resolve metal by adding inorganic acid solution (sulfuric acid); for the sake of helping the efficiency of reaction, the controlling condition therefor is to heat up to make the temperature raised to 95° C. and to control the PH value to be below 0.3. The inorganic acid added therein, in addition to sulfuric acid, can be but is not limited to chlorhydric acid or hydrobromic acid.

The adding of oxidant mainly is to oxide $Fe^{+2}$ to form $Fe^{+3}$ for helping the neutralization step in a subsequent stage; the oxidant added includes but is not limited to potassium manganate, hydrogen peroxide, nitric acid, or introduced ozone or air.

The first time filtering uses a filtering device to separate solid material and liquid; the method of filtering includes but is not limited to bag type filtering, plate type filtering, cross-flow filtering, centrifugation filtering, Dorr type, hydracyclone or hyperflux type filtering.

Figure 6:
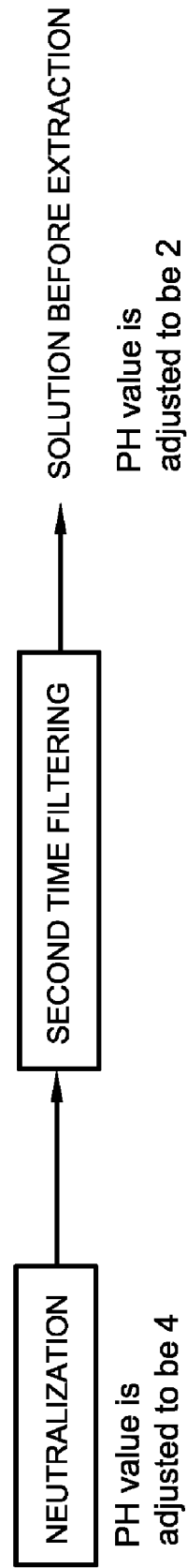
FIG. 6 is a process flow diagram showing the step of neutralization and sedimentation step in the method of purifying and regenerating of catalyst of the present invention.

Referring to FIG. 6, the neutralization and sedimentation step includes neutralization and second time filtering to form solution before extraction with an object of removing much iron (Fe) ions.

During neutralization, the controlling condition therefor is to adjust the PH value to be 4 in order to eliminate $Fe^{+3}$, thereby the acid solution step shall be added therein oxidant in advance, because:

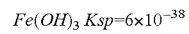
$Fe(OH)_3$ $Ksp=6\times10^{-38}$

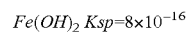
$Fe(OH)_2$ $Ksp=8\times10^{-16}$

The chemical reaction formula is:

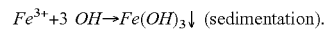
$Fe^{3+}+3\ OH^-\rightarrow Fe(OH)_3\downarrow$ (sedimentation).

The method of second time filtering includes but is not limited to bag type filtering, plate type filtering, cross-flow filtering, centrifugation filtering, Dorr type, hydracyclone or hyperflux type filtering etc. for forming solution before extraction.

In the resin treatment step, resin is used to remove copper, nickel and chromium ions, the chemical reaction formula is:

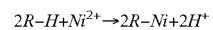
$2R-H+Ni^{2+}\rightarrow 2R-Ni+2H^+$

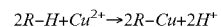
$2R-H+Cu^{2+}\rightarrow 2R-Cu+2H^+$

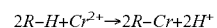
$2R-H+Cr^{2+}\rightarrow 2R-Cr+2H^+$

The flow rate of resin for removing copper, nickel and chromium ions is very important, it will influence the efficiency of adsorption. Better flow rate for practicing is 0.5 eq/litter of resin; this can get 100% efficiency of adsorption. Besides, inorganic acid is used for the purpose of regenerating the resin, the inorganic acid is but is not limited to chlorhydric acid or hydrobromic acid or sulfuric acid.

The metal extraction step uses organic extractant to remove zinc and iron ions, the chemical reaction formula is:

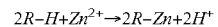
$2R-H+Zn^{2+}\rightarrow 2R-Zn+2H^+$

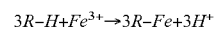
$3R-H+Fe^{3+}\rightarrow 3R-Fe+3H^+$

And inorganic acid can be used for regeneration; wherein inorganic acid is but is not limited to chlorhydric acid or hydrobromic acid or sulfuric acid etc.; while the extractant can be 2-ethylhexyl phosphate, butyl-dibutyl phosphonate or sec-octyl phenoxyl acid.

In the electrolyzing step, ammoniac salt is added to the amount of 1-10%, and most preferably 3% before electrolyzing to form complex ions for preventing sedimentation of cobalt ions ($Co^{2+}$), the chemical reaction formula is:

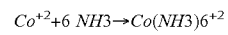
$Co^{+2}+6\ NH3\rightarrow Co(NH3)6^{+2}$

By virtue that during electrolyzing in an electrolyzing tank, the anode will acidify and shall have PH value adjusted to avoid further resolving the electrolyzed cobalt. The PH value is controlled at 3-6 inorganic alkali, and most preferably at 4 for controlling further resolving of the electrolyzed cobalt solution. Wherein the inorganic alkali includes but is not limited to sodium hydroxide or potassium hydroxide. The voltage for electrolyzing is 3-5 V, the current is smaller than 8000 A. When the weight percentage of cobalt in electrolyzing is reduced to be smaller than 0.2%, the waste electrolyzing solution is discharged to a low cobalt content treatment area, till the concentration of cobalt become less than 10 ppm and then the waste electrolyzing solution is discharged to a waste water treatment area.

Referring to FIG. 7, the cobalt purifying/regenerating system 11 designed according to the method of the present invention is applied to the PTA manufacturing process as shown in FIG. 1 to recover catalyst. The cobalt purifying/regenerating system 11 includes: an acid solution device 112, a first filtering device 113, a neutralization device 114, a second filtering device 115, a resin treatment device 116, an extraction device 117 and an electrolyzing device 118.

The cobalt containing inorganic acid solution recovered by the PTA mother liquid recovering system 50 is passed through the acid solution device 112, then inorganic acid (sulfuric acid) is added to resolve metal. By separating solid material from liquid with the first filtering device 113, the liquid obtained is sent into the neutralization device 114; the PH value is adjusted to be 4 in order to eliminate iron ions. The liquid is passed through the second filtering device 115 to form solution before extraction. The solution before extraction is sent into the resin treatment device 116 to remove copper, nickel and chromium ions; and then is sent into the extraction device 117, organic extractant is used to remove zinc and iron ions; and then is sent into the electrolyzing device 118 to obtain metal cobalt.

The obtained metal cobalt with high purity and extremely few impurities is sent into the oxidized catalyst producing system 12 to produce oxidized catalyst which can be circulated for reusing.

The catalyst purifying/regenerating system 10 of the present invention is characterized in:

1. the neutralization step to eliminate iron ions;

2. the resin treatment step to remove copper, nickel and chromium ions;

3. the metal extraction step to remove zinc and iron ions;

4. the electrolyzing step by which metal cobalt obtained is separated from the ion impurities of sodium (Na), potassium (K), calcium (Ca), magnesium (Mg), manganese (Mn), sulfuric acid group ($SO_4^{2-}$) ammoniac salt (NH3) etc. for manufacturing metal cobalt of high purity and low impurity, then the metal cobalt is used to produce oxidized catalyst with a CMB oxidized catalyst purifying/regenerating system, the oxidized catalyst is circulated for reusing;

5. by electrolyzing, metal cobalt with better purity and fewer impurities is regenerated;

6. In the conventional chemical method in recovering catalyst, there is no method to separate the catalyst discharged from the ion impurities, this makes accumulation of the impurities; the present invention uses a chemical method to remove impurities in the first place, and then make regeneration by electrolyzing, this is the first innovative method in the art.

The embodiment stated above is only for illustrating the present invention, and not for giving any limitation to the scope of the present invention. It will be apparent to those skilled in this art that various modifications or changes can be made to the elements of the present invention without departing from the spirit, and scope of this invention. Accordingly, all such modifications and changes also fall within the scope of the appended claims and are intended to form part of this invention.

The invention claimed is:

1. A method for recovering PTA (purified terephthalic acid) mother liquid and purifying and regenerating catalyst, said method includes following steps:
    a) said PTA mother liquid is filtered for separating solid organic materials from liquid;
    b) said liquid separated is heated, and is passed through a heat exchanger to raise its temperature for 5-10° C. to increase solubility of said organic materials in water;
    c) cobalt ions in said mother liquid are adsorbed with anion exchange resin till being saturated;
    d) said resin is regenerated with inorganic alkali, when there is organic material attached to surfaces of granules of said resin during exchanging of anion exchange resin, said inorganic alkali is used to regenerate said resin to remove said organic material on said surfaces;
    e) inorganic acid is used to take off by changing over all said cobalt ions adsorbed by said resin to form inorganic acid solution containing cobalt; and
    f) catalyst is purified and regenerated to convert said inorganic acid solution into metal cobalt which is then used to produce oxidized catalyst for a process of manufacturing (purified terephthalic acid) PTA, wherein said step to convert said inorganic acid solution into metal cobalt further includes steps:
        f-1) an acid solution step to resolve metal by adding inorganic acid solution;
        f-2) a neutralization and sedimentation step to adjust pH value to be 4 in order to eliminate iron ions and to form solution before extraction;
        f-3) a resin treatment step to use resin to remove copper, nickel and chromium ions in said solution before extraction in advance;
        f-4) a metal extraction step to use organic extractant to remove zinc and iron ions in said solution before extraction; and
        f-5) an electrolyzing step after extraction to obtain metal cobalt by electrolyzing said solution before extraction.

2. The method for recovering PTA (purified terephthalic acid) mother liquid and purifying and regenerating catalyst as claimed in claim 1, wherein waste water created in adsorbing said cobalt ions with said anion exchange resin is purified with reverse osmotic waste water treating system, said waste water with increased concentration is discharged to a waste water pool for treating, regenerated water is generated after purification and is circulated for reusing.

3. The method for recovering PTA (purified terephthalic acid) mother liquid and purifying and regenerating catalyst as claimed in claim 1, wherein said step of filtering and separating said PTA mother liquid is chosen from: bag type filtering, plate type filtering, cross-flow filtering, centrifugation filtering, Dorr type, hydracyclone or hyperflux type filtering.

4. The method for recovering PTA (purified terephthalic acid) mother liquid and purifying and regenerating catalyst as claimed in claim 3, wherein filtrant for said PTA mother liquid for filtering and separating is chosen from: terephthalic acid, o-phthalic acid, iso-phthalic acid, benzoic acid, p-toluic acid or 4-carboxyl benzaldehyde.

5. The method for recovering PTA (purified terephthalic acid) mother liquid and purifying and regenerating catalyst as claimed in claim 1, wherein said resin in said anion exchange resin is chosen from: strong acidic anion exchange resin, weak acidic anion exchange resin or chelate resin.

6. The method for recovering PTA (purified terephthalic acid) mother liquid and purifying and regenerating catalyst as claimed in claim 1, wherein said inorganic acid is chosen from: chlorhydric acid, hydrobromic acid or sulfuric acid.

7. The method for recovering PTA (purified terephthalic acid) mother liquid and purifying and regenerating catalyst as claimed in claim 1, wherein said inorganic alkali is chosen from: sodium hydroxide, potassium hydroxide or sodium carbonate.

8. The method for recovering PTA (purified terephthalic acid) mother liquid and purifying and regenerating catalyst as claimed in claim 1, wherein residues of crude terephthalic acid (CTA) are recovered with a crude terephthalic acid (CTA) residue recovering system to make solid metal salt; and a PTA mother liquid recovering system is used to recover said PTA (purified terephthalic acid) mother liquid to produce cobalt containing inorganic acid solution.

9. The method for recovering PTA (purified terephthalic acid) mother liquid and purifying and regenerating catalyst as claimed in claim 8, wherein said acid solution step includes adding of oxidant to oxide $Fe^{+2}$ to form $Fe^{+3}$ for helping said neutralization step in a subsequent stage; and includes first time filtering to separate solid material and liquid.

10. The method for recovering PTA (purified terephthalic acid) mother liquid and purifying and regenerating catalyst as claimed in claim 1, wherein controlling condition for said acid solution is to heat up to make temperature raised to 95° C. and to control pH value to be below 0.3.

11. The method for recovering PTA (purified terephthalic acid) mother liquid and purifying and regenerating catalyst as claimed in claim 1, wherein said inorganic acid solution added is chosen from chlorhydric acid or hydrobromic acid in addition to said sulfuric acid.

12. The method for recovering PTA (purified terephthalic acid) mother liquid and purifying and regenerating catalyst as claimed in claim 9, wherein said oxidant added is chosen from potassium manganate, hydrogen peroxide, nitric acid, or introduced ozone or air.

13. The method for recovering PTA (purified terephthalic acid) mother liquid and purifying and regenerating catalyst as claimed in claim 9, wherein said first time filtering method is chosen from: bag type filtering, plate type filtering, cross-flow filtering, centrifugation filtering, Dorr type, hydracyclone or hyperflux type filtering.

14. The method for recovering PTA (purified terephthalic acid) mother liquid and purifying and regenerating catalyst as claimed in claim 1, wherein said neutralization and sedimentation step includes:
neutralization in which $OH^-$ is added to make sedimentation of $Fe^3$ to get $Fe(OH)_3$; and includes
second time filtering to have said sedimented $Fe(OH)_3$ filtered to form said solution before extraction with an object of removing much iron (Fe) ions.

15. The method for recovering PTA (purified terephthalic acid) mother liquid and purifying and regenerating catalyst as claimed in claim 14, wherein said second time filtering is chosen from: bag type filtering, plate type filtering, cross-flow filtering, centrifugation filtering, Dorr type, hydracyclone or hyperflux type filtering.

16. The method for recovering PTA (purified terephthalic acid) mother liquid and purifying and regenerating catalyst as claimed in claim 14, wherein pH value of said solution before extraction is adjusted to 2-4.

17. The method for recovering PTA (purified terephthalic acid) mother liquid and purifying and regenerating catalyst as claimed in claim 1, in said resin treatment step, flow rate of resin for removing copper, nickel and chromium ions if 0.5 eq/litter of resin that gets 100% efficiency of adsorption.

18. The method for recovering PTA (purified terephthalic acid) mother liquid and purifying and regenerating catalyst as claimed in claim 17, in said resin treatment step, inorganic acid is used for regeneration; said inorganic acid is chosen from: chlorhydric acid or hydrobromic acid or sulfuric acid.

19. The method for recovering PTA (purified terephthalic acid) mother liquid and purifying regenerating catalyst as claimed in claim 17, in said metal extraction step, said extractant is 2-ethylhexyl phosphate, butyl-dibutyl phosphonate or sec-octyl phenoxyl acid.

20. The method for recovering PTA (purified terephthalic acid) mother liquid and purifying and regenerating catalyst as claimed in claim 17, in said metal extraction step, said inorganic acid is used for regeneration, and is chosen from: chlorhydric acid or hydrobromine acid or sulfuric acid.

21. The method for recovering PTA (purified terephthalic acid) mother liquid and purifying and regenerating catalyst as claimed in claim 1, in said electrolyzing step, ammoniac salt is added to an amount of 1-10% to form complex ions for preventing sedimentation of cobalt ions ($Co^{2+}$).

22. The method for recovering PTA (purified terephthalic acid) mother liquid and purifying and regenerating catalyst as claimed in claim 1, wherein during electrolyzing in an electrolyzing tank, pH value is controlled at 3-6 with inorganic alkali, and most preferably at 4, for controlling further resolving of electrolyzed cobalt solution.

23. The method for recovering PTA (purified terephthalic acid) mother liquid and purifying and regenerating catalyst as claimed in claim 22, in said electrolyzing step, said inorganic alkali is chosen from: sodium hydroxide or potassium hydroxide.

24. The method for recovering PTA (purified terephthalic acid) mother liquid and purifying and regenerating catalyst as claimed in claim 1, in said electrolyzing step, voltage for electrolyzing is 3-5 V, current is smaller than 8000 A.

25. The method for recovering PTA (purified terephthalic acid) mother liquid and purifying and regenerating catalyst as claimed in claim 1, in said electrolyzing step, when weight percentage of cobalt in electrolyzing is reduced to be smaller than 0.2%, waste electrolyzing solution is discharged to a low cobalt treatment area, till concentration of cobalt becomes less than 10 ppm and then said waste electrolyzing solution is discharged to a waste water treatment area.

26. The method for recovering PTA (purified terephthalic acid) mother liquid and purifying and regenerating catalyst as claimed in claim 1, wherein metal cobalt obtained by electrolyzing is sent into an oxidized catalyst producing system to produce oxidized catalyst.

* * * * *